(12) United States Patent
McLean

(10) Patent No.: US 7,179,297 B2
(45) Date of Patent: Feb. 20, 2007

(54) COMBINED BIPOLAR AND UNIPOLAR TRIALS

(75) Inventor: Terry W. McLean, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 10/245,855

(22) Filed: Sep. 17, 2002

(65) Prior Publication Data
US 2004/0054421 A1    Mar. 18, 2004

(51) Int. Cl.
*A61F 2/32* (2006.01)
*A61F 2/36* (2006.01)

(52) U.S. Cl. ............... 623/22.11; 623/22.12; 623/23.11

(58) Field of Classification Search ............. 623/22.12, 623/22.11, 22.15, 22.19, 22.21, 22.28, 22.29, 623/22.2, 18.11, 23.11; 606/80
See application file for complete search history.

(56) References Cited

U.S. PATENT DOCUMENTS

| 3,813,699 | A |   | 6/1974  | Giliberty                    |
|-----------|---|---|---------|------------------------------|
| 4,135,517 | A |   | 1/1979  | Reale                        |
| 4,528,980 | A |   | 7/1985  | Kenna                        |
| 4,676,799 | A | * | 6/1987  | Legrand ............. 623/22.19 |
| 4,770,658 | A |   | 9/1988  | Geremakis                    |
| 4,770,659 | A | * | 9/1988  | Kendall ............. 623/22.19 |
| 4,936,855 | A | * | 6/1990  | Sherman ............. 623/22.2 |
| 5,049,158 | A | * | 9/1991  | Engelhardt et al. ....... 623/22.25 |
| 5,156,626 | A | * | 10/1992 | Broderick et al. ........ 623/22.12 |
| 5,176,711 | A |   | 1/1993  | Grimes                       |
| 5,507,826 | A | * | 4/1996  | Besselink et al. ......... 623/22.29 |
| 5,658,348 | A | * | 8/1997  | Rohr, Jr. ............. 623/22.29 |
| 5,800,556 | A |   | 9/1998  | Sanders et al.               |
| 5,879,401 | A |   | 3/1999  | Besemer et al.               |
| 5,888,211 | A |   | 3/1999  | Sanders                      |
| 5,964,809 | A | * | 10/1999 | Lin et al. ............. 264/257 |

FOREIGN PATENT DOCUMENTS

| EP | 0140642   |   | 10/1984 |
|----|-----------|---|---------|
| GB | 2001247   | A | 7/1978  |

\* cited by examiner

*Primary Examiner*—Pedro Philogene
(74) *Attorney, Agent, or Firm*—Fulbright & Jaworski LLP

(57) ABSTRACT

The present invention is directed to a set of trial prosthesis instrumentation for use in trial fitting of a medical implant such as a femoral hip prosthesis. The two piece set provides a combined bipolar and unipolar trial prosthesis instrumentation and comprises an outer component and a inner component. The outer component comprises an exterior surface characterized by a substantially hemispherical shape to correspondingly mate with a joint socket and an interior surface characterized by a substantially hemispherical shape, and an inner component that comprises an exterior surface that comprises a surface and that is shaped to correspondingly mate with the interior surface of the outer component and an interior surface characterized by a substantially columnar shape that correspondingly mates with a prosthetic stem. Methods of use are also contemplated.

13 Claims, 5 Drawing Sheets

COMBINED BIPOLAR AND UNIPOLAR TRIALS

TECHNICAL FIELD

The present invention is related to the field of medicine, particularly to the field of orthopedics. The invention provides a trial prosthesis comprising an outer component and an inner component compatible with the outer component, and may be utilized in either a bipolar or a unipolar hemiarthroplasty in which the proximal portion of the femur is replaced with a suitable prosthetic hip joint implant or implant assembly which articulates directly with the natural acetabulum.

BACKGROUND OF THE INVENTION

A successful hip replacement or arthroplasty procedure results, in part, from selection of prosthetic joint components that are dimensioned and positioned to closely approximate or replicate the geometry and functional characteristics of a natural, healthy hip joint. Typically, the component selection process includes a pre-operative analysis of joint images. The component selection process also includes temporary fixation of one or more provisional components to a bone or bones of interest prior to permanent fixation of the prosthetic joint. The provisional components are intended to mimic certain aspects of the permanent prosthetic joint in order for a surgeon to validate measurements and to test several different component sizes and configurations. Hence, provisional components are aptly known as "trials."

Two different types of procedures are typically suitable for hemiarthroplasty procedures. Briefly, hemiarthroplasty is a surgical procedure in which a joint is partially replaced, i.e., the natural acetabulum is retained in the hip joint of the patient. One of these types is the use of a bipolar prosthesis member (for example, see U.S. Pat. No. 3,813,699 to Giliberty and U.S. Pat. No. 4,770,658 to Geremakis et al.). In general, a bipolar prosthesis has an external surface which articulates with the natural acetabulum and an internal surface which articulates with the spherical head member of a prosthetic femoral component. The other of these types is often referred to as a unipolar endoprosthesis in which the prosthetic femoral component includes a spherical head member which is large enough to articulate directly with the natural acetabulum. Both of the above hemiarthroplasty procedures enable articulation with the natural acetabulum.

These two procedures permit later conversion to a total hip replacement in which the acetabular portion is also replaced with a prosthetic acetabular component. With the bipolar procedure, the bipolar prosthesis is removed from the head of the hip stem, and an acetabular prosthesis is implanted which mates with the head of the remaining femoral component. With the unipolar endoprosthesis, the head is typically a separate component from the stem portion of the hip prosthesis. This permits the larger unipolar head to be removed and replaced with a smaller head without removing the femoral stem to enable the smaller head to mate with an acetabular prosthetic implant component Determining the fit of a prosthesis or medical implant before implantation is generally accomplished using a trial prosthesis instrumentation. An example of a femoral prosthesis trial fitting device is described in U.S. Pat. No. 4,135,517 and corresponding application GB 2001247 to Reale, which disclose a trial head 30 and a bearing insert which removably fits within the trial head. The bearing insert may be removably mountable on either a femoral prosthesis stem or a trial handle.

U.S. Pat. No. 5,879,401 to Besemer et al. describes an acetabular trial system comprising an outer shell and an inner shell for placement within the outer shell that are rotatably fixed with a pin about a transverse axis that extends through the outer shell and that defines a range of anteversion angels, wherein the transverse axis is perpendicular to a sagittal plane of a patient's body. This trial system allows for the determination of an appropriate anteversion angle for the acetabular cup of the hip prosthesis. U.S. Pat. No. 4,528,980 and corresponding application EP 0140642 to Kenna describe an acetabulum sizer for properly sizing an acetabulum prior to receiving an acetabular cup prosthesis comprising a substantially hemispherical shell having an outside surface that generally conforms to the outside surface of the prosthesis, a circular peripheral rim, a handle means for manipulating the shell, wherein the shell is characterized by having viewing ports to enable visual inspection of the acetabulum during sizing.

In an effort to simplify the trial process of a surgical procedure and expand the utility of conventional trial prosthesis instrumentation, combined bipolar and unipolar trial instrumentation were explored. For example, related U.S. Pat. No. 5,800,556 and U.S. Pat. No. 5,888,211 to Sanders et al. describe a bipolar to unipolar head trial adapter that may be inserted into or removed from a bipolar shell to convert the bipolar shell to a unipolar head. The adapter comprises a two piece system that provides an adjustable neck to eliminate the necessity for multiple unipolar head trials corresponding to different neck lengths for each of the different possible head sizes. U.S. Pat. No. 5,156,626 describes a multiple piece set of provisional instrumentation for a hemiarthroplasty that includes a common outer shell that releasably mates with two different types of inner components, wherein the combination of the shell and the first inner component is used for a bipolar procedure and the combination of the shell and the second inner component is used for a unipolar procedure.

The present invention further simplifies the trial instrumentation employed in trial fitting of a medical implant (i.e., joint prosthesis) by providing a two-piece trial prosthesis instrumentation for use in either a bipolar or a unipolar surgical procedure.

BRIEF SUMMARY OF THE INVENTION

The present invention is directed to a system and method that describe and provide a trial prosthesis instrumentation for use in trial fitting of a medical implant. One embodiment of the present invention provides a combined bipolar and unipolar trial hip prosthesis instrument that includes an outer component as the bipolar trial and an inner component that is releasably inserted into the outer component to convert the bipolar trial to a unipolar trial.

Another embodiment of the invention is to provide a set of surgical hip instrumentation comprising a single style outer shell component for use as a bipolar prosthesis trial for hemiarthroplasty, and an inner (insert) component that removably fits into the outer component to provide an assembly for use as a unipolar endoprosthesis for hemiarthroplasty.

A further embodiment of the invention is to provide such an outer component that is also used as an acetabular sizing gauge.

A still further embodiment of the invention is to provide a set of trial hip prosthesis instrumentation comprising a common style outer component is used with an interchangeable style of an inner (insert) component, the set is useful for different types of surgical procedures and reduces inventory and manufacturing costs thereof.

Another embodiment of the invention is to provide a femoral trial system comprising a plurality of sizes of outer components and a plurality of sizes of mating inner components, each of which are used in a trial fitting of a medical implant.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

Figure 1:
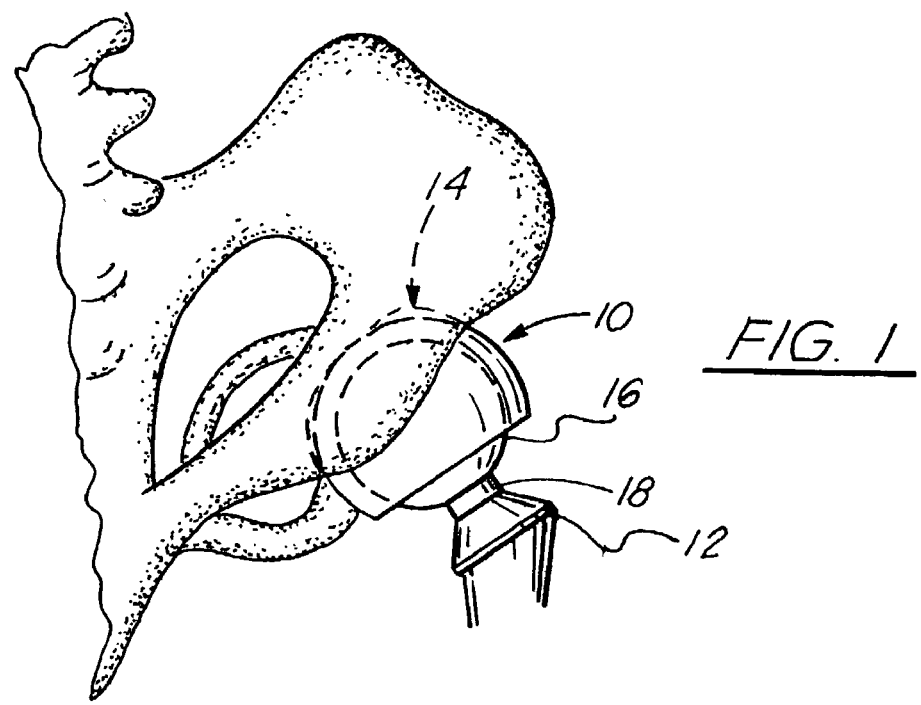
FIG. 1 is a partial perspective view illustrating a hip joint including a prosthetic device.

LIST OF DESIGNATIONS FOR THE COMPONENTS IN DRAWINGS 5 bipolar trial prosthesis
7 unipolar trial prosthesis
10 hip prosthesis
12 prosthesis stem
14 acetabulum socket
16 prosthesis head
18 prosthesis neck
20 outer component
22 exterior of outer component
24 interior of outer component
25 apical opening of outer component
26 shape of interior surface of outer component
27 split ring
28 annular groove in interior of outer component
30 inner component
32 exterior of inner component
34 interior of inner component
35 interior shape of inner component
36 annular groove in exterior of inner component
38 surface of inner component
40 space between surface of inner component and interior surface of outer component
42 annular groove in interior of inner component
43 spacing means
44 peripheral rim of inner component

DETAILED DESCRIPTION OF THE INVENTION

FIGS. 1–7 illustrate a particularly advantageous embodiment of a set of trial instrumentation of the present invention. The invention is described with reference to preparing a hip prosthesis 10 using trial prosthesis instrumentation for a hip joint, such as illustrated in FIG. 1, and more particularly to the acetabulum 14. However, it is understood that this description does not constitute a limitation upon the scope of the invention and that the principles of the invention may be suitable and applicable for other joints, such as the shoulder or the like and is equally applicable in veterinary uses.

Figure 2:
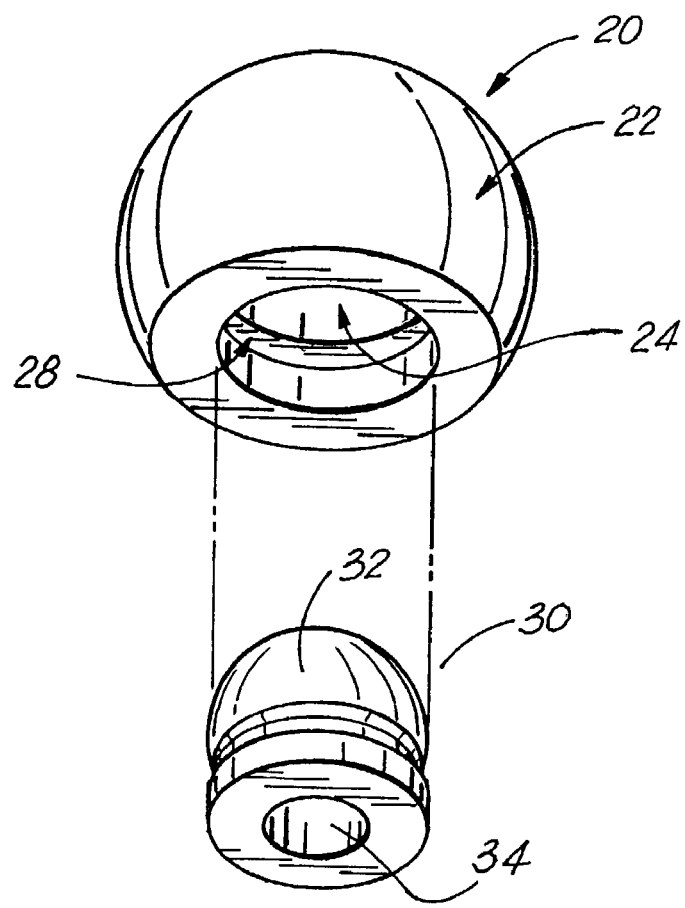
FIG. 2 is an exploded perspective view of an outer component and an inner component according to the present invention.

The set of trial prosthesis instrumentation exemplified in FIG. 2 is suitable for use in a trial fitting of a medical implant, such as is necessary with a hemiarthroplasty femoral hip replacement. The set comprises an outer component 20 and an inner component 30. The outer component 20 includes an exterior surface 22 characterized by a substantially hemispherical shape to correspondingly mate with a joint socket, and an interior surface 24. The inner component 30 includes an exterior surface 32, which is shaped to correspondingly mate with the interior surface 24 of outer component 20 and has a surface 38 (FIG. 4), and an interior surface 34 characterized by a substantially columnar shape 35 therein. The inner component 30 is selectively inserted into the outer component 20 in mating contact with the interior surface 24 of outer component 20.

Figure 3A:
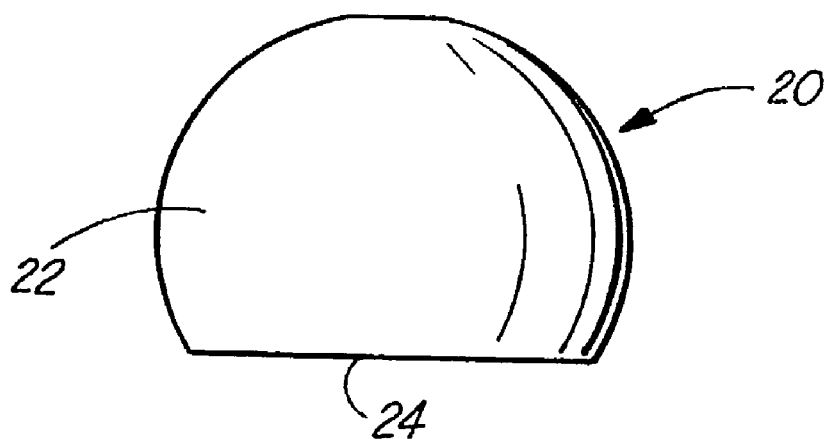
FIGS. 3A and 3B are a side view (A) and a cross-sectional view (B) of an outer component trial.
Figure 3B:
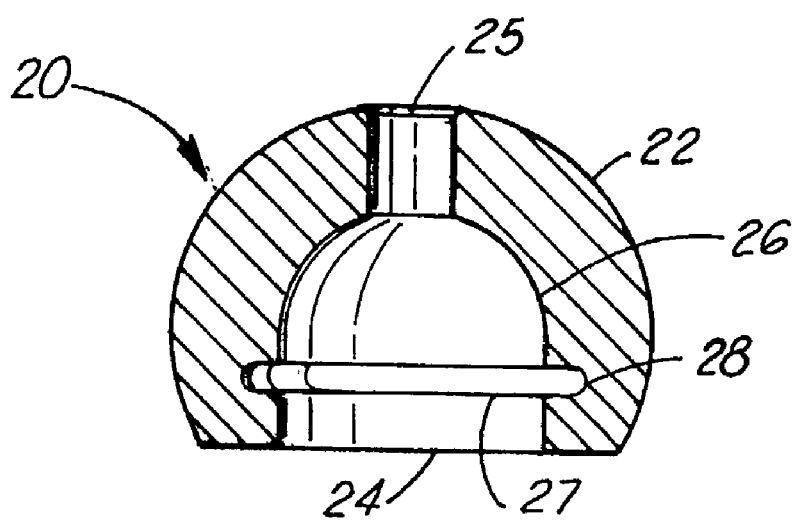

The interior surface 24 of the outer component 20 comprises a substantially hemispherical shape 26 therein (FIGS. 3A and 3B). This shape 26 of the interior surface 24 enables the outer component 20 to mate with a corresponding substantially hemispherical shaped provisional head 16 on stem 12 via neck 18 on stem 12. It is noted that the trial outer component 20 may be utilized for trial fitting with the natural acetabulum during surgery in conjunction with such a trial provisional stem 12 and provisional head 16 combination. Alternatively, the outer component 20 may be used with the actual implant stem and head. Thus, the assembly 5 (shown in FIG. 6) is utilized as a trial in conjunction with a bipolar surgical procedure.

Figure 7:
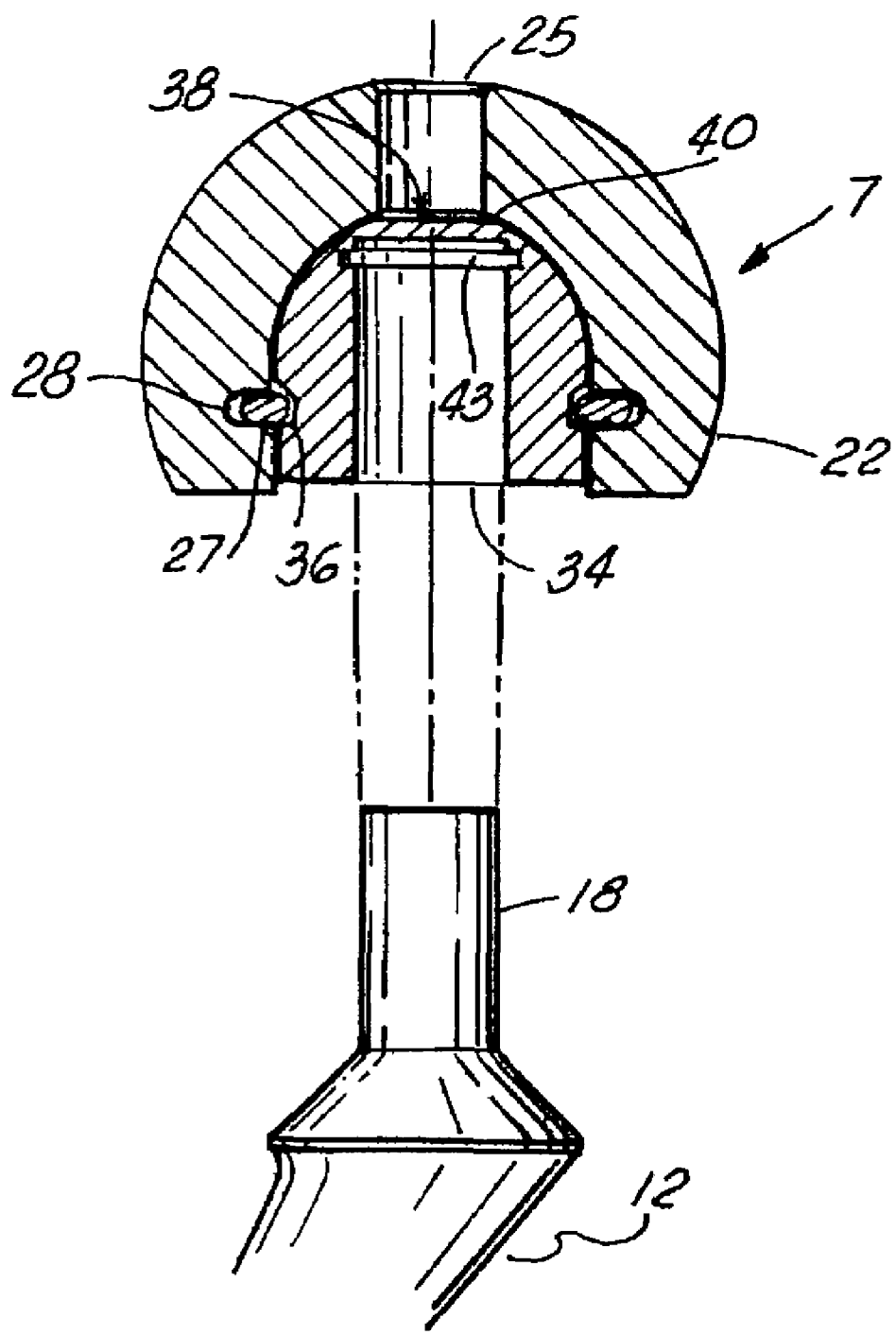
FIG. 7 is an exploded view including a cross-sectional view of the outer component trial assembled with a provisional head, shown with a side view of a corresponding provisional hip stem.

The shape 26 of the interior surface 24 also enables the outer component 20 to mate with inner component 30. If inner component 30 is selectively inserted into the outer component 20 in mating contact with the interior surface 24 of outer component 20, the assembly 7 (FIG. 7) provides a unipolar trial prosthesis. The configuration of the interior surface 34 of the inner component 30 comprises a substantially columnar shape as designated by 35 in FIGS. 5 and 7. This substantially columnar shape 35 of the interior surface 34 enables the inner component 30 to mate with a provisional stem 12 via a correspondingly shaped neck 18 on stem 12, as shown in FIG. 7. The columnar shape 35 of the interior surface 34 need not be symmetric, provided the columnar shape 35 of the interior surface 34 is shaped to mate with the corresponding neck 18. For example, the columnar shape 35 may be tapered so as to fit a conventional neck trial prosthesis, which may also be tapered. One of ordinary skill in the art is aware of common taper dimensions (i.e., diameter of the neck measured at two different points along its length) that are well-known in the art. It is noted that the trial inner component 30 in combination with a corresponding provisional or trial outer component 20 may be utilized for trial fitting with the natural acetabulum during surgery in conjunction with such a trial or provisional stem 12, such as is illustrated in FIG. 7. Alternatively, the inner component 30 and outer component 20 assembly 7 may be used with the actual implant stem. Thus, the assembly 5″ (shown in FIGS. 5 and 7) which includes outer component 20 and inner component 30, is utilized as a unipolar trial prosthesis in conjunction with a unipolar surgical procedure. It is noted that the inner component 30 has a surface 38, and, thus, when inner component 30 is correspondingly mated with the interior surface 24 of the outer component 20, a space 40 is formed that may be accessed via apical opening 25 in outer component 20. The apical opening 25 together with surface 38 allows access of a blunt instrument and a platform by which the inner component 30 is pushed out of outer component 20. This disassembly is achieved by inserting the blunt instrument through apical opening 25 and applying a force to the surface 38 via the blunt instrument to disengage inner component 30 from outer component 20.

Figure 5:
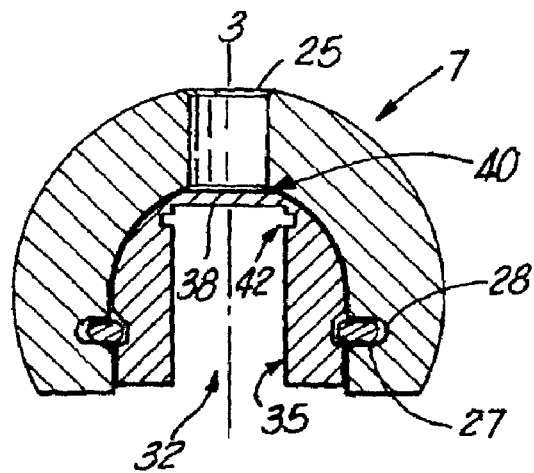
FIG. 5 is a cross-sectional view of the inner unipolar component assembled with the outer component trial.
Figure 6:
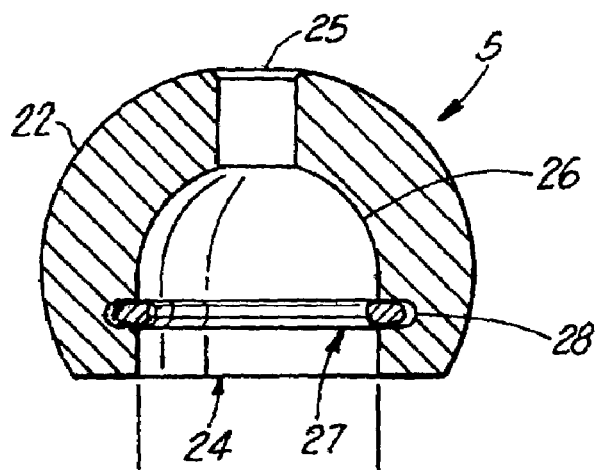
FIG. 6 is an exploded view including a cross-sectional view of the outer component assembled with the inner component, shown with a side view of a corresponding provisional hip stem and related provisional head.

The cross-sectional shape of the interior surface 24 of outer component 20 and the exterior surface 32 of inner component 30 may be substantially U-shaped, as shown in FIGS. 3B and 5, although any suitable corresponding, mating interior surface 24 and exterior surface 32 may be utilized. The corresponding interior surface 24 and exterior surface 32 is sized to slide releasably in and out in frictional engagement with each other, with a slip-fit, friction fit, mechanical release, or other suitable equivalent known to those of skill in the art, between the outer component 20 and inner component 30. Manual pressure may be all that is required to slide the inner component 30 into or out of outer component 20. Finger pressure will connect the inner component 30 with the corresponding outer component 20.

Figure 4:
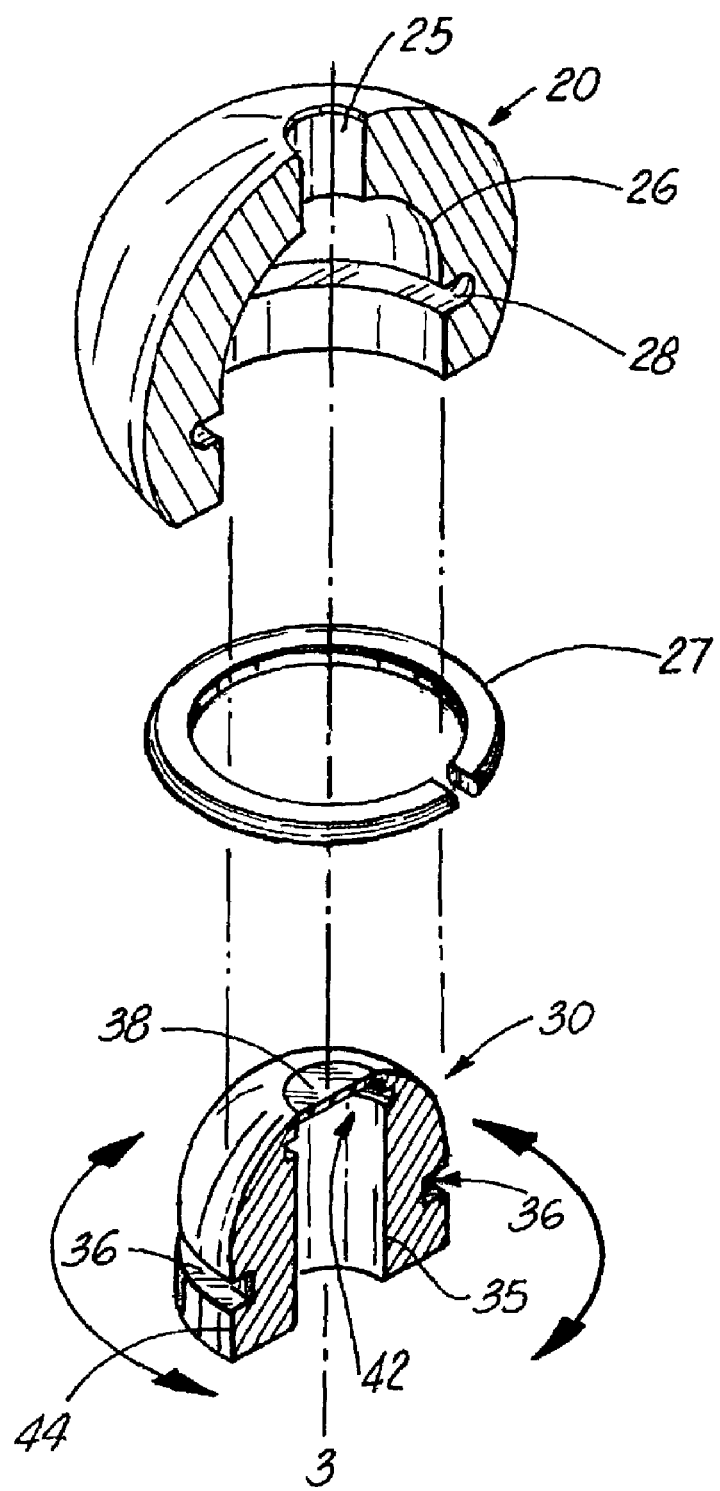
FIG. 4 is an elevated view of the connecting elements of a unipolar trial of the present invention.

The outer component 20 further comprises an annular groove 28 about the interior surface 24 as shown in FIGS. 4 and 5. A resilient split ring 27 is retained in the annular groove 28 and maintained by a biased spring force. The inner surface of the split ring 27 has a dual chamfer, as shown in FIG. 4, to maintain the inner component 30 in outer component 20. The split ring 27 is expandable and thus recedes further into the annular groove 28 upon insertion of the inner component 30. The frictional pressure of split ring 27 against the exterior surface 32 of inner component 30 provides a positive lock that maintains the inner component 30 in outer component 20 until the user releases the inner component 30 back out to release it from the outer component 20.

It is also noted that the inner component 30 may include an annular groove 36 on the exterior surface 32 that is located to correspond to split ring 27 on the interior surface 24 of outer component 20 (FIG. 4). The annular groove 36 of inner component 30 provides a recessed area in which the split ring 27 expands and recedes to further maintain the inner component 30. The annular groove 36 also forms a peripheral rim 44 around the base of the exterior surface 32 of inner component 30. The peripheral rim 44 does not protrude beyond the edge of exterior surface 32.

To disassemble the inner component 30 from the outer component 20, outer component 20 is held while the interior surface 34 of inner component 30 is gripped with finger pressure and pulled out. Depending on the size of the interior surface 34 of the inner component 30, it may be difficult to grip in this manner, thus it is contemplated that a blunt instrument may be used, as described above, to disassemble the inner component 30 from the outer component 20.

The set of combined bipolar and unipolar trial prosthesis instrumentation as described herein may include a plurality of outer components 20 of varying sizes and/or a plurality of inner components 30 of varying sizes. The varying sizes are not shown in the accompanying figures, but it is understood that sizing may vary and that mating components have corresponding/mating sizing features as desired.

The use of the trial assembly 5 for a bipolar trial fitting with the acetabulum requires that the correct size of outer component 20 must be selected. The exterior surface 22 of outer component 20 includes a hemispherical portion of a sphere, although more than half of a sphere may be provided, as shown in the Figures. It is important to match the exterior shape of outer component 20 as accurately as possible with the shape of the natural acetabulum.

Further, the interior surface 34 of inner component 30 may have an annular groove or recessed area 42 proximal to the opening of the interior (FIG. 7). The groove 42 may be fitted with suitable spacing means 43 to maintain snug fit in th prosthesis stem 12. Non-limiting examples of such spacing means may be annular rings, multiple mating tapers, o-rings, gaskets, ball detents, etc. One of ordinary skill in the art recognizes that any of these examples or other equivalent components may be used for this purpose The spacing means 43 expands and thus recedes into the recessed area 42 upon insertion of the neck 18 of provisional stem member 12. The spacing means 43 facilitates a snug contact and mate between the provisional prosthesis stem 12 with the neck 18 of stem 12 even where dimensions of the neck 18 vary from a trial to a permanent prosthesis or among different manufacturers who may have different standards for measuring or sizing the neck 18. The interior surface 34 having the annular groove 42 fitted with means 43 of inner component 30 is dimensioned to releasably fit over correspondingly shaped neck 18.

In use, the surgeon determines whether a bipolar hemiarthroplasty procedure (in which case outer components 20 are used) or a unipolar hemiarthroplasty procedure (in which case the combination of outer components 20 and inner components 30 are used) is to be performed. Again, the present invention enables the user to use a common style outer trial component 20 with an inner trial component 30 to adapt the trial system for a different type of surgical procedure. Alternatively, the outer component 20, which is used in the trial assembly of 5 and/or 7, may be used without an inner component as an acetabular gauge to size the natural acetabulum for trial fitting a medical implant thereto. Specifically in use in a hemiarthroplasty, the outer component 20 is positioned against the acetabulum to observe the fit therebetween. Thus, the exterior surface 22 of outer component 20 is bone-contacting. If there is not good mating contact with the outer component 20 and acetabulum, another outer component 20 with a different size exterior surface 22 is selected. This process is continued until an outer component 20 with the desired fit between the exterior surface 22 and the acetabulum is determined. After the correct outer component 20 is chosen, a provisional substantially spherical head member 16 (or the like spherical implant head member) is inserted into the interior surface 24 of outer component 20. Upon insertion, the split ring 27 expands and thus recedes into recessed area 28. Once the head passes split ring 27, the ring contracts to its rest position capturing the head 16 in the interior 24 of outer component 20.

Alternatively, if the surgeon desires to perform a unipolar trial fitting, the appropriate outer component 20 is selectively chosen as described above and then the desired mating size of the inner component 30 is selected. The selected inner component 30 is then inserted into the selected outer component to form a unipolar trial prosthesis for use in a unipolar trial fitting.

If outer component 20 is selected for a bipolar trial fitting, this trial assembly 5 provides trial dual joint articulation, with articulation about exterior surface 22 of outer component 20 against the natural acetabulum, and with articulation about interior surface 24 of outer component 20 about head 16. Alternatively, if inner component 30 is selected for use with outer component 20 for a unipolar trial fitting, this trial prosthesis instrument also provides dual articulation, with articulation about exterior surface 22 of outer component 20 against the natural acetabulum, and with restricted articulation about interior surface 24 of outer component 20 about exterior surface 32. The restricted articulation about interior surface 24 of outer component 20 about exterior surface 32 results from a free rotation about a vertical center axis 3, i.e., spinning, of inner component 30 (FIGS. 4 and 5) while in mating contact with the interior surface 24 of outer component 20.

The components of the present invention are made in accordance with any suitable manufacturing practices. Additionally, any suitable material useful for temporary surgical use may be utilized. Examples of such suitable materials include, but are not limited to a variety of copolymers and plastics, such as polyoxymethylene which is generally known as Celcon®, polyetherimide, polyethylene, polypropylene, polyphenyl sulfone, which is commercially known as Radel®, nylon and mixtures thereof, a metal, such as aluminum and stainless steel or other suitable materials that are well-known in the art. It is further understood that any suitable material may be utilized for any of the components. For those components the are resilient, any material that possess shape memory may be used including, for example, polymeric and/or metallic materials such as acetal copolymer, polyethylene, polypropylene and nylon.

The various sizes of outer components 20 and inner components 30 may vary in accordance with the surgical needs. For example, the outer components 20 may be provided with various external diameters. External diameters typically may run incrementally from 30 mm to 72 mm, although the sizes are not limited thereto. The external diameter of the various sizes of outer components 20 correspond to the various sizes of the outer diameters of the bipolar implant components or to the various sizes of the outer diameter of the unipolar endoprosthesis heads, which are to be selected for implantation. In general, the sizing of trial prostheses is designed to correlate with the corresponding prosthetic components to be implanted. The inner hemispherical surface 26 of outer component 20 and/or the exterior surface 32 of inner component 30 may vary in accordance with the corresponding sizes of spherical head members with which it will mate. Examples of typical size ranges for the diameter for the inner hemispherical surface 26 are 22 mm, 28 mm and 32 mm, although the sizing is not limited thereto. The inner surface 34 of inner component 30 is basically sized to releasably slide on and off a corresponding neck member of a stem such as 12 via the neck 18. The interior of the various outer components 20 are sized and shaped to correspond with the exteriors of any mating size of inner components 30. The size of the substantially columnar inner region 34 of inner component 30 may vary in accordance with the corresponding sizes of columnar neck members such as 18 with which it will mate. Alternatively, a sleeve may be inserted into the substantially columnar shape 35 of interior surface 34 of inner component 30 to vary accordingly the size of the interior surface 34 as desired. Sleeves suitable for the purpose of varying and/or adjusting the size of an acetabular trial include, for example, neck taper sleeves. Other suitable equivalents, known to those of ordinary skill in the art, may also be used.

A set of trial instrumentation in accordance with the embodiments described and illustrated herein may be provided as specific to size. For example, the inner component 30 is provided with the respective outer component 20 to which it correspondingly mates. For example, an outer component 20 with an interior surface 24 having an inner size A corresponds and mates with inner component 30 having an exterior surface 32 having an outer size A. The dimensions of inner size A and outer size A are suitably designed to releasably mate together, as previously described. Accordingly, inner size B mates with outer size B, inner size C with outer size C, and inner size D with outer size D. Thus, in certain embodiments, the present invention provides a femoral trial system comprising a plurality of outer components, each characterized by a specific size of the interior surface 24 or of the exterior surface 22. In further embodiments, the femoral trial system further comprises a plurality of inner components, each characterized by a specific size of the interior surface 34 or of the exterior surface 32.

For the convenience of the user, each of the plurality of outer components and/or each of the plurality of inner components may be color-coded, such as according to the specific size. For example, the inner size A and outer size A components are all red, so that any red inner component 30 will mate correctly with any red outer component 20. Accordingly, all size B's are black, all size C's are white, and all size D's are blue. It is understood that the color-coding may be varied as desired. Further, it is recognized that certain variations in the mating scheme may be suitable in systems and methods of the present invention. For example, an inner component 30 having an outer size D may be indicated to mate with a 60 and a 63 mm outer components 20 comprising inner size D. However, any outer size D component could mate with any inner size D component. Therefore, it is understood that the outer size D inner component 30 could actually mate with the other inner size D outer components too.

The present invention enables selective attachment of inner trial components with outer trial components to provide a set of trial prosthesis. The trial components are adapted and styled for two different types of surgical procedures. While this invention has been described and exemplified, in terms of a particularly advantageous embodiment, those skilled in the art can appreciate that modification can be made without departing from the spirit and scope of this invention Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

U.S. Pat. No. 3,813,699
U.S. Pat. No. 4,135,517
U.S. Pat. No. 4,528,980
U.S. Pat. No. 4,770,658
U.S. Pat. No. 5,156,626
U.S. Pat. No. 5,176,711
U.S. Pat. No. 5,800,556
U.S. Pat. No. 5,879,401
U.S. Pat. No. 5,888,211
EP 140642
GB 2001247

What is claimed is:

1. A set of trial prosthesis instrumentation for use in trial fitting of a medical implant consisting essentially of a single outer component and a single inner component, wherein the outer component comprises an exterior surface characterized by a substantially hemispherical shape to correspondingly mate with a joint socket and an interior surface characterized by a substantially hemispherical shape, said interior surface of said outer component having a size and shape to directly mate with said inner component when used for unipolar trials and to directly mate with a provisional head component when used for bipolar trials, wherein said inner component comprises an exterior surface that is shaped to correspondingly mate with the interior surface of the outer component and an interior surface characterized by a substantially columnar shape that correspondingly mates with a prosthetic stem for unipolar trials, wherein said single inner component comprises a peripheral rim to permit no more than restricted articulation between said single inner component and said single outer component.

2. The product of claim 1, wherein the interior surface of the outer component further comprises an annular groove and a split ring retained therein.

3. The product of claim 2, wherein the exterior surface of the inner component further comprises an annular groove that when the inner component is selectively inserted into the outer component, said split ring expands into said annular groove.

4. A method of trial fining a medical implant to a patient comprising determining a size of the implant for the patient comprising the step of using a set of trial prosthesis instrumentation, said trial prosthesis instrumentation consisting essentially of a single outer component and a single inner component, wherein the outer component comprises an exterior surface characterized by a substantially hemispherical shape to correspondingly mate with a joint socket and an interior surface characterized by a substantially hemispherical shape, said interior surface of said outer component having a size and shape to directly mate with said inner component when used for unipolar trials and to directly mate with a provisional head component when used for bipolar trials, wherein said inner component comprises an exterior surface that is shaped to correspondingly mate with the interior surface of the outer component and an interior surface characterized by a substantially columnar shape that correspondingly mates with a prosthetic stem for unipolar trials, wherein said single inner component comprises a peripheral rim to permit no more than restricted articulation between said single inner component and said single outer component.

5. The method of claim 4, wherein the outer component is used in direct mating contact with a provisional head component in a bipolar trial fitting.

6. The method of claim 4, wherein the interior surface of the outer component further comprises an annular groove and a split ring retained therein.

7. The method of claim 6, wherein the exterior surface of the inner component further comprises an annular groove that when the inner component is selectively inserted into the outer component, said split ring expands into said annular groove.

8. The method of claim 4, further comprising the step of selectively inserting the inner component into the outer component in mating contact with the interior surface of the outer component in a unipolar trial fitting.

9. A femoral trial system comprising:
a plurality of sets of trial prosthesis instrumentation, wherein each set of said plurality of sets consists essentially of a single outer component having an interior surface of a specific size and a single inner component,
wherein said outer component comprises an exterior surface characterized by a substantially hemispherical shape to correspondingly mate with a joint socket and an interior surface characterized by a substantially hemispherical shape, said interior surface of said outer component having a size and shape to directly mate with said inner component when used for unipolar trials and to directly mate with a provisional head component when used for bipolar trials,
wherein said inner component comprises an exterior surface shaped and sized to correspondingly mate with the interior surface of the outer component and an interior surface characterized by a substantially columnar shape that correspondingly mates with a prosthetic stem for unipolar trials, wherein said single inner component comprises a peripheral rim to permit no more than restricted articulation between said single inner component and said single outer component.

10. The femoral trial system of claim 9, wherein the interior surface of the outer component further comprises an annular groove and a split ring retained therein.

11. The femoral trial system of claim 10, wherein the exterior surface of the inner component further comprises an annular groove that when the inner component is selectively inserted into the outer component, said split ring expands into said annular groove.

12. The femoral trial system of claim 9, wherein the outer component is color-coded with respect size.

13. The femoral trial system of claim 9, wherein the inner component is color-coded with respect size.

* * * * *